United States Patent
Nagai et al.

(10) Patent No.: US 7,816,116 B2
(45) Date of Patent: Oct. 19, 2010

(54) MODIFIED CREATININE AMIDE HYDROLASE HAVING IMPROVED AFFINITY FOR SUBSTRATE, AND REAGENT COMPOSITION FOR DETERMINATION OF CREATININE

(75) Inventors: Rie Nagai, Tsuruga (JP); Masao Kitabayashi, Tsuruga (JP); Yoshiaki Nishiya, Tsuruga (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 0 days.

(21) Appl. No.: 12/297,572

(22) PCT Filed: Apr. 20, 2007

(86) PCT No.: PCT/JP2007/058594

§ 371 (c)(1),
(2), (4) Date: Oct. 17, 2008

(87) PCT Pub. No.: WO2007/125824

PCT Pub. Date: Nov. 8, 2007

(65) Prior Publication Data

US 2009/0170145 A1    Jul. 2, 2009

(30) Foreign Application Priority Data

| Apr. 25, 2006 | (JP) | ............................. 2006-120313 |
| Sep. 13, 2006 | (JP) | ............................. 2006-247681 |
| Nov. 9, 2006 | (JP) | ............................. 2006-303451 |

(51) Int. Cl.
- *C12N 9/00* (2006.01)
- *C12N 9/78* (2006.01)
- *C12N 1/20* (2006.01)
- *C12N 15/00* (2006.01)
- *C07H 21/04* (2006.01)

(52) U.S. Cl. .................... 435/227; 435/183; 435/252.3; 435/320.1; 536/23.2

(58) Field of Classification Search .................. None
See application file for complete search history.

(56) References Cited

U.S. PATENT DOCUMENTS

2003/0119084 A1    6/2003    Shao et al.

FOREIGN PATENT DOCUMENTS

| EP | 0 402 929 A1 | 6/1990 |
| JP | 3-19690 A | 1/1991 |
| JP | 2003-180352 A | 7/2003 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Beuth et al., *Journal of Molecular Biology*, 332(1): 287-301 (2003).
Yoshimoto et al., *Journal of Molecular Biology*, 337(2): 399-416 (2004).
Yamamoto et al., *Biosci. Biotech. Biochem.*, 59(7): 1331-1332 (1995).

* cited by examiner

*Primary Examiner*—Christian L Fronda
(74) *Attorney, Agent, or Firm*—Leydig, Voit & Mayer, Ltd.

(57) ABSTRACT

To overcome disadvantages of a known creatinine amide hydrolase, and provide a creatinine amide hydrolase having improved affinity for creatinine or having a decreased Km value for creatinine, and also provide a reagent composition for use in the determination of creatinine, which is adapted to an automated analysis apparatus and is excellent in accuracy, preciseness and economic efficiency.

Disclosed is a modified creatinine amide hydrolase having improved affinity for a substrate compared to an unmodified one. Also disclosed is a creatinine determination reagent comprising the modified creatinine amide hydrolase, a creatinine amidino hydrolase, sarcosine oxidase and a reagent for detection of hydrogen peroxide.

19 Claims, 1 Drawing Sheet

MODIFIED CREATININE AMIDE HYDROLASE HAVING IMPROVED AFFINITY FOR SUBSTRATE, AND REAGENT COMPOSITION FOR DETERMINATION OF CREATININE

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 6,731 bytes ASCII (Text) file named "703792SequenceListing.txt," created Oct. 17, 2008.

TECHNICAL FIELD

The present invention relates to a modified creatinine amide hydrolase (also expressed as creatinine amidohydrolase) having improved affinity for a substrate, a gene encoding the modified creatinine amide hydrolase, a method for producing the modified creatinine amide hydrolase, and various applications of the modified creatinine amide hydrolase in creatinine determination reagents.

BACKGROUND ART

Rapid and accurate detection and determination of creatinine, which is found in blood or urine, are very important for diagnosis of diseases such as uremia, chronic nephritis, acute nephritis, gigantism, and tonic muscular dystrophy.

A creatinine amide hydrolase (EC 3.5.2.10) has been used as an enzyme for determination of creatinine in body fluids, which is an indicator in clinical diagnosis of muscular and renal diseases, together with other enzymes such as creatine amidinohydrolase, sarcosine oxidase and peroxidase. A creatinine amide hydrolase is an enzyme which acts on creatinine to catalyze a reversible reaction of the formation of creatine from creatinine in the presence of water.

Such a creatinine amide hydrolase is known to be produced by microorganisms of the genera *Pseudomonas* (non-Patent Document 1) and *Alcaligenes* (non-Patent Document 2). In addition, as other producers of a creatinine amide hydrolase, only microorganisms of the genera *Flavobacterium, Corynebacterium, Micrococcus* (Patent Document 1), *Penicillium* (Patent Document 2), etc. are known. Among them, a gene encoding a creatinine amide hydrolase produced by *Pseudomonas putida* PS-7 was already isolated, and the amino acid sequence thereof has been published (Patent Document 3).

non-Patent Document 1: Journal of Biochemistry, Vol. 86, 1109-1117 (1979)

non-Patent Document 2: Chemical and Pharmaceutical Bulletin, Vol. 34, No. 1, 269-274 (1986)

Patent Document 1: JP 51-115989 A

Patent Document 2: JP 47-43281 A

Patent Document 3: Japanese Patent 2527035

However, the creatinine amide hydrolase produced from various known microorganisms had a large Km value to creatinine as an enzyme for a clinical-test and thus, a greater amount of the enzyme should be added to a reagent composition. For example, an enzyme derived from *Alcaligenes faecalis* TE3581 (Patent Document 4) is reported to have a Km value to creatinine of about 42 mM. Another enzyme derived from *Arthrobacter* sp. TE1826 has a larger Km value to creatinine of about 66 mM (Patent Document 5).

Patent Document 4: JP 9-154574 A

Patent Document 5: JP 10-215874 A

For quantitative determination of creatinine, known is a method of quantitatively determining creatinine in a sample by treating the creatinine in the sample with creatinine amide hydrolase, creatine amidinohydrolase and sarcosine oxidase and determining the resulting hydrogen peroxide by a hydrogen peroxide-determining means.

For carrying out such a method, a universally applicable automatic analyzer is often used, wherein a concentration of an objective substance is determined by dividing reagents into two or more portions, adding the portions one by one in a predetermined addition order to a reaction cell to react the portions for about several minutes to about 20 minute as the entire steps, monitoring an increase and a decrease in absorbance over time during the period, and analyzing and calculating the results. There are various known reagents that can be used in these automatic analyzers.

Non-patent Document 3: Medical Technology, Vol. 10, No. 7, 575-579 (1982)

However, in conventional methods, since it takes a longer period of time until the reaction reaches the end point, the number of samples to be analyzed is limited. On the other hand, for completion of the reaction in a short period of time, an amount of an enzyme to be added should be raised, which has caused an economical problem.

● : Preparation of the present invention

○ : Preparation of Comparative Example

Figure 2:
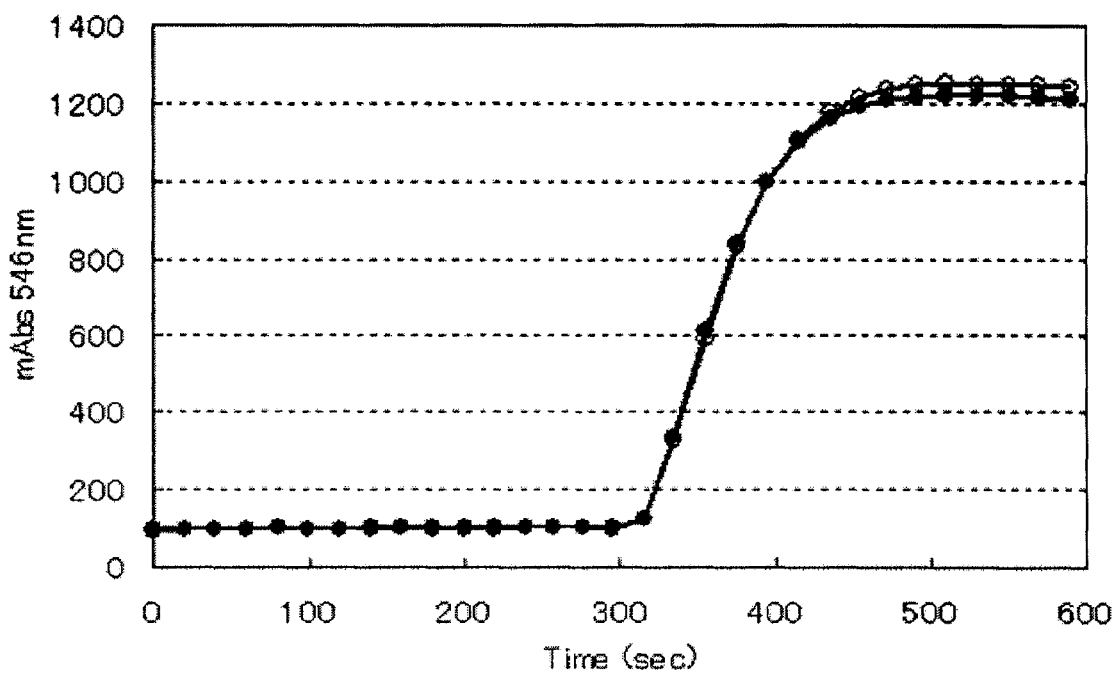

FIG. 2 illustrates the results of reactivity of evaluation of the reagent of present invention and the reagent of Comparative Example.

● : Preparation of the present invention

○ : Preparation of Comparative Example

DISCLOSURE OF THE INVENTION

Problems to be Solved by the Invention

An object of the present invention is to provide a creatinine amide hydrolase, as mentioned above, overcoming disadvantages of known creatinine amide hydrolase and having improved affinity for creatinine, i.e., having a smaller Km value to creatinine.

Further, in view of the above circumstances, another object of the present invention is to provide a reagent composition for use in the determination of creatinine, which is adapted to an automatic analyzer and excellent in accuracy, preciseness and economic efficiency.

Means of Solving the Problems

After intensive studies to achieve the above objects, the present inventors have succeeded in the creation of a modified creatinine amide hydrolase having a smaller Km value to creatinine by using a gene of the above creatinine amide hydrolase of *Pseudomonas putida* origin in accordance with a protein engineering technique. The present inventors have also found that, in quantitative determination of creatinine, the period of time required to reach the reaction end point becomes shorter as a decrease in the Km value of a creatinine amide hydrolase. Thus, the present invention has been completed.

That is, the construction of the present invention is as follows:

[Item 1]

A modified creatinine amide hydrolase having improved affinity for a substrate as compared with the affinity before modification, wherein amino acid(s) within a distance in radius of 10 angstroms from a binding site to the substrate and within five residues from both α-helix terminals in an amino acid sequence constituting a protein having an unmodified creatinine amide hydrolase activity is modified by deletion, substitution or addition of one to several amino acids.

[Item 2]
The modified creatinine amide hydrolase according to the item 1, wherein at least one amino acid in the amino acid sequence constituting a protein having an unmodified creatinine amide hydrolase activity is substituted with amino acid(s) other than those of a wild-type one.

[Item 3]
The modified creatinine amide hydrolase according to any one of the items 1 and 2, which has 50% or more homology to an amino acid sequence of SEQ ID No. 2 in the Sequence Listing.

[Item 4]
The modified creatinine amide hydrolase according to any one of the items 1 and 2, which has 80% or more homology to an amino acid sequence of SEQ ID No. 2 in the Sequence Listing.

[Item 5]
The modified creatinine amide hydrolase according to any one of the items 1 and 2, wherein the protein having an unmodified creatinine amide hydrolase activity has the amino acid sequence of SEQ ID No. 2 in the Sequence Listing.

[Item 6]
The modified creatinine amide hydrolase according to any one of the items 3 to 5, wherein at least one amino acid at the position selected from the group consisting of 44th, 122nd, 179th, 180th, and 181st positions in an amino acid sequence represented by SEQ ID No. 2 in the Sequence Listing or position(s) equivalent thereto is substituted with other amino acid(s).

[Item 7]
The modified creatinine amide hydrolase according to any one of the items 3 to 5, wherein glycine at the 179th position of the amino acid sequence of SEQ ID No. 2 in the Sequence Listing or a position equivalent thereto is substituted with serine.

[Item 8]
The modified creatinine amide hydrolase according to any one of the items 3 to 5, wherein glycine at the 179th position of the amino acid sequence of SEQ ID No. 2 in the Sequence Listing or a position equivalent thereto is substituted with alanine.

[Item 9]
The modified creatinine amide hydrolase according to any one of the items 3 to 5, wherein glycine at the 180th position of the amino acid sequence of SEQ ID No. 2 in the Sequence Listing or a position equivalent thereto is substituted with alanine.

[Item 10]
The modified creatinine amide hydrolase according to any one of the items 1 to 9, wherein the Km value to creatinine after modification is 1/5 or less as compared with that before modification.

[Item 11]
The modified creatinine amide hydrolase according to any one of the items 1 to 9, wherein the Km value to creatinine after modification is 1/2.5 or less as compared with that before modification.

[Item 12]
A gene encoding the modified creatinine amide hydrolase according to any one of the items 1 to 9.

[Item 13]
A vector comprising the gene according to the item 12.

[Item 14]
A transformant transformed with the vector according to the item 13.

[Item 15]
A method for producing a modified creatinine amide hydrolase which comprises culturing the transformant according to the item 14 and collecting a creatinine amide hydrolase from the culture.

[Item 16]
A reagent for determination of creatinine, comprising the modified creatinine amide hydrolase according to any one of the items 1 to 11.

[Item 17]
A method for determining creatinine which comprises using the modified creatinine amide hydrolase according to any one of the items 1 to 11.

EFFECTS OF THE INVENTION

According to the present invention, it is possible to create a novel creatinine amide hydrolase useful as an enzyme for a clinical-test reagent and having a smaller Km value and to produce the creatinine amide hydrolase industrially in a large amount.

Also according to the present invention, it is possible to reduce the amount of the enzyme used in quantitative determination of creatinine to ¼ of the conventional amount and to shorten the period to the reaction end point if used in the same amount as the conventional amount, thus shortening the determination period and increasing the number of samples to be analyzed.

BEST MODE FOR CARRYING OUT THE INVENTION

Hereinafter, the present invention will be described in detail.

A creatinine amide hydrolase is an enzyme classified in EC 3.5.2.10.

The modified creatinine amide hydrolase of the present invention has improved affinity for a substrate as compared with an unmodified creatinine amide hydrolase. Improvement in the affinity for a substrate means a decrease in the Km value to creatinine.

The modified creatinine amide hydrolase of the present invention is preferably a modified creatinine amide hydrolase whose Km value to creatinine after modification is 1/2.5 or less as compared with that before modification. More preferably, it is a modified creatinine amide hydrolase whose Km value to creatinine after modification is 1/5 or less as compared with that before modification.

Alternatively, the modified creatinine amide hydrolase of the present invention is preferably a modified creatinine amide hydrolase whose Km value to creatinine after modification (as determined by the method shown hereinafter) is 70 mM or less. More preferably, it is a modified creatinine amide hydrolase whose Km value to creatinine after modification is 55 mM or less.

Alternatively, the modified creatinine amide hydrolase of the present invention has 50% or more (preferably 80% or more) homology to the amino acid sequence of SEQ ID No. 2 in the Sequence Listing.

The Km value is determined by one of the following methods.

Regarding Examples 1 to 3, the Km value was determined in the following manner:

In the method of determining the activity of creatine amide hydrolase described hereinafter, R2 is adjusted so that the concentration of the substrate, creatinine, becomes 55.6, 37.0, 22.2, 15.9 or 11.1 mM at the time of reaction, and the activity is measured by using each R2. The Km value is determined by a Lineweaber-Burk plotting of the data thus measured.

Further, regarding the Km value in Examples 4 and 5 was determined in the following manner:

In the method of measuring the activity of creatine amide hydrolase described hereinafter, the second reagent is adjusted so that the concentration of the substrate, creatinine, becomes 50, 30, 20, 15 or 10 mM (error of ±10% is allowable) at the time of reaction, and the activity of the enzyme is measured by using each R2. The Km value is determined by a Lineweaber-Burk plotting of the data thus measured.

Herein, each amino acid is expressed by a single character code or a three letter code. The position of amino acid mutation is expressed by the following manner: For example, "G179S" means substitution of G (Gly) at the 179th position with S (Ser).

Examples of a creatinine amide hydrolase to be modified, from which the modified creatinine amide hydrolase of the present invention is obtained, include that originated from microorganisms of the genera *Corynebacterium, Pseudomonas, Arthrobacter, Flavobacterium, Micrococccus*, or the like, but is not particularly limited thereto.

Specific examples include that originated from *Pseudomonas putida* (PS-7) strain, whose amino acid sequence is represented by SEQ ID No. 2, and the gene encoding the amino acid sequence is represented by SEQ ID No. 1. Each of these sequences is described in Japanese Patent No. 2527035. The amino acids in the SEQ ID No. 2 are numbered by taking methionine as 1.

A creatinine amide hydrolase to be modified, from which the modified creatinine amide hydrolase of the present invention is obtained, is not limited to a wild type one, and a creatinine amide hydrolase having certain modification can also be used as far as it has a creatinine amide hydrolase activity. Examples of such modification include deletion, substitution or addition of amino acids, intermolecular or intramolecular crosslinking, chemical modification with a sugar chain or other functional groups, or the like, but is not particularly limited.

Specifically, an enzyme of the genus *Pseudomonas* or *Alcaligenes* origin or, a commercially available product such as "CNH-311" produced by Toyobo Co., Ltd., "Creatininase (C1-E)" produced by Kikkoman Corporate, etc. can be modified.

The modified creatinine amide hydrolase of the present invention has improved affinity for a substrate as compared with a wild type one, wherein amino acid(s) within a distance in radius of 10 angstroms from a binding site to the substrate and within five residues from both α-helix terminals in an amino acid sequence constituting a protein having an unmodified creatinine amide hydrolase activity is modified by deletion, substitution or addition of one to several amino acids. The binding site to the substrate is defined by conformational data using Swiss-Pdb Viewer (SPDBV) of the creatinine amide hydrolase binding to creatine. The distance from the binding site to the substrate can also be determined by using the same software.

Specific examples of such modification sites include, in the case of the amino acid sequence of the creatinine amide hydrolase *Pseudomonas putida* (PS-7) strain origin (SEQ ID No. 2), Cys41, Met42, Asn43, Val44, Asp45, His120, Tyr121, Asn123, Ser124, Asp155, Glu177, His178, Gly179, Gly180, and Val181.

Among them, an creatinine amide hydrolase obtained by substitution of at least one amino acid corresponding to the 44th, 122nd, 179th, 180th, and 181st positions with other amino acid(s) is preferable as the modified creatinine amide hydrolase of the present invention.

In particular, the amino acid at the 44th position of SEQ ID No. 2 is preferably substituted with arginine, glycine or serine.

The amino acid at the 44th position of SEQ ID No. 2 is preferably substituted with asparagine.

The amino acid at the 122nd position of SEQ ID No. 2 is preferably substituted with aspartic acid.

The amino acid at the 179th position of SEQ ID No. 2 is preferably substituted with serine or alanine.

The amino acid at the 180th position of SEQ ID No. 2 is preferably substituted with serine or alanine.

The amino acid at the 181st position of SEQ ID No. 2 is preferably substituted with isoleucine.

Among the sites corresponding to the 44th, 122nd, 179th, 180th, and 181st positions, amino acids at the 122nd, 179th, 180th, and 181st positions are preferably substituted with other amino acids. Further, more preferably, the amino acids at the 179th and 180th positions are substituted with other amino acids.

The modification site(s) may be one to several sites. Further, the modification may be any of deletion, substitution or addition of amino acids, or may be a combination thereof.

The above substitution site may be a position equivalent thereto in an amino acid sequence of a creatinine amide hydrolase other than that of *Pseudomonas putida* (PS-7) strain origin. Whether or not a position is that equivalent thereto can be determined based on knowledge of its primary and conformational structure.

Although the conformational structure of the creatinine amide hydrolase of *Pseudomonas putida* origin was elucidated, there was no description showing that the Km value of a creatinine amide hydrolase can be decreased by a protein-engineering technique (non-Patent Documents 4 and 5).

non-Patent Document 4: Journal of Molecular Biology, Vol. 337, 399-416 (2004)

non-Patent Document 5: Journal of Molecular Biology, Vol. 332, 287-301 (2004)

When the mutation sites at the 44th, 122nd, 179th, 180th, and 181st positions in the creatinine amide hydrolase of *Pseudomonas putida* origin found by the present inventors were compared to the conformational structure, it was found that the 44th and 122nd positions are located within 5 residues from the α-helix terminals, and the 179th, 180th and 181st positions are located within the flag region.

Non-Patent Document 3 describes that the conformational structure of the creatinine amide hydrolase is composed of seven α-helix structures and four β structures and the binding between the creatinine amide hydrolase and the substrate causes configuration change in the flap region (between α5 and α6 structures).

When this description is combined with the experimental results specifically obtained by the present inventors, it is considered that the change in the structure between α5 and α6 structures leads to configuration change in the flap region to improve affinity for the substrate.

Therefore, those skilled in the art can obtain without excess studies a modified enzyme having an improved effect in affinity for a substrate by modifying amino acids not only the 44th, 122nd, 179th, 180th and 181st positions, but also in the surrounding region thereof (specifically, amino acids within five residues from the α5 and α6 terminals in the flap region, and further, in addition to the flap region, amino acids close to the binding site to the substrate, specifically amino acids within five residues from the α-helix terminal and within a distance of 10 angstroms) to cause configuration change in the flap region.

It is also possible to estimate the amino acid position(s) to be modified in a creatinine amide hydrolases from other origins based on information of its primary and conformational structure to obtain a modified enzyme having an improved effect in affinity for the substrate without excess studies.

Thus, the technological idea of the present invention is not particularly limited to the modified creatinine amide hydrolase obtained above.

In the above-mentioned explanation, the binding site to the substrate is a site defined from conformational structure data by using Swiss-Pdb Viewer (SPDBV) of the creatinine amide hydrolase in the binding state with creatine. The distance from the binding site to the substrate can also be determined by using the same software.

The α-helix used herein is one of secondary structures of a protein or a polypeptide, and is a helical structure having a pitch of 5.4 angstroms formed by the amino acid chain helically rotating itself in every 3.6 amino acid residues. The peptide bonds therein are on a plane, and —$NH_2$— and —CO— therein all form hydrogen bonds.

The homology can be determined as an identical sequence rate (%) by homology search between two kinds of sequences by using GENETYX-WIN.

In the modified creatinine amide hydrolase of the present invention, a part of other amino acid residues in the sequence may further be deleted, substituted, or inserted, or other amino acid residues may be added or substituted as far as the activity to creatinine is substantially maintained.

Further, the modified creatinine amide hydrolase of the present invention may include, as far as the activity to creatinine is substantially maintained, an aspect wherein a tag such as a histidine tag is bonded or inserted into the creatinine amide hydrolase, an aspect wherein another peptide or another protein (e.g., streptavidin or cytochrome) is fused with at least one terminal of the creatinine amide hydrolase, an aspect wherein the enzyme is modified with a sugar chain or another compound, and an aspect wherein the creatinine amide hydrolase is cross-linked by a disulfide bond, or the like intramolecularly and/or intermolecularly, or an aspect wherein the enzymes are coupled via a linker peptide. Furthermore, the enzyme of the present invention may also include that composed of combination of fragments of some wild-type creatinine amide hydrolases.

The present invention also includes a gene encoding the modified creatinine amide hydrolase.

The gene encoding the modified creatinine amide hydrolase of the present invention can be obtained, for example, by modifying a DNA fragment containing a gene encoding a wild-type creatinine amide hydrolase obtained from various sources (origins) such as microorganisms. Specific examples thereof include bacteria such as *Alcaligenes faecalis, Arthrobacter* sp., *Flavobacterium* sp., *Corynebacterium ureafaciens, Corynebacterium creatinovorans, Micrococcus luteus,* and *Pseudomonas putida.*

The gene encoding the modified creatinine amide hydrolase of the present invention is preferably a DNA that hybridizes with a DNA having a nucleotide sequence complementary to the nucleotide sequence represented by SEQ ID No. 1 under stringent conditions and encodes a protein having creatinine amide hydrolase activity.

The gene of the present invention may also include a gene obtained by further modification of Codon usage in a gene encoding a modified creatinine amide hydrolase obtained by modification of a gene encoding a wild-type creatinine amide hydrolase so that the expression amount of the creatinine amide hydrolase is improved.

As a method for modifying the gene encoding a wild-type creatinine amide hydrolase, a conventional method for modifying genetic information can be employed. That is, a DNA having genetic information of a modified protein is prepared by modifying a particular base of the DNA having the genetic information of the protein, or inserting or deleting a particular base to or from the DNA. Specific examples of the method for modifying a particular base in a DNA include, for example, use of a commercially available kit (e.g., Transformer Site-directed Mutagenesis Kit; produced by Clonetech, Quick Change Site Directed Mutagenesis Kit; produced by Stratagene) or use of a polymerase chain reaction (PCR) method.

The present invention also includes a vector containing the gene encoding the modified creatinine amide hydrolase, and further, a transformant transformed with the vector.

The DNA having the genetic information of the modified protein thus constructed is incorporated into a host microorganism in a state that it is connected to a plasmid, giving a transformant producing the modified protein. For example, when *Escherichia coli* is used as a host microorganism, a plasmid such as pBluescript or pUC18 can be used as the vector. Examples of the host microorganisms include *Escherichia coli* W3110, *Escherichia coli* C600, *Escherichia coli* JM109, *Escherichia coli* DH5α and the like. For introduction of the recombinant vector into the host microorganism, for example, a recombinant DNA can be incorporated in the presence of calcium ions, or alternatively by electroporation, in case that the host microorganism is *Escherichia coli*. Further, a commercially available competent cell (e.g., Competent High M109; produced by Toyobo Co., Ltd.) can be used.

Such a gene can be extracted from these strains or synthesized chemically. Further, DNA fragments containing the creatinine amide hydrolase gene can be obtained by using a PCR method.

In the present invention, the gene encoding the creatinine amide hydrolase can be obtained, for example, by the following method. A chromosome of, for example, *Pseudomonas putida* (PS-7) strain origin is isolated, purified, and cleaved by ultrasonication, a restriction enzyme treatment, etc. to obtained a DNA fragment, and it is bonded to a linear expression vector at the blunt ends or the cohesive ends of both DNAs by treatment with a DNA ligase, etc., followed by closing a ring to construct a recombinant vector. A microorganism containing the recombinant vector having the gene encoding the creatinine amide hydrolase is obtained by introducing the recombinant vector into a replicable host microorganism, and screening by using a marker of the vector marker and the expressed enzyme activity as indicators.

Then, the microorganism containing the above-mentioned recombinant vector is cultured, and the recombinant vector is isolated and purified from the cells of the cultured microorganism, thereby collecting a gene encoding the creatinine amide hydrolase from the expression vector. Specifically, for example, the chromosomal DNA of *Pseudomonas putida* (PS-7), i.e., the gene donor, can be collected in the following manner.

The gene-donor microorganism is cultured with stirring, for example, for 1 to 3 days, the culture obtained is centrifuged to collect the cells, and the cells are subjected to lysis to give a lysate containing a creatinine amide hydrolase gene. As a lysis method, for example, the cells are treated with a lytic enzyme such as lysozyme and, if necessary, a protease and other enzymes and a surfactant such as sodium dodecylsulfate (SDS) are used in combination. Further, a physical pulverization means such as freeze thawing or a French press processing can be used in combination.

The isolation and purification of a DNA from the lysate thus obtained can be carried out, for example, by appropriately combining a protein removal treatment such as a phenol treatment or a protease treatment, with a ribonuclease treatment, an alcohol-precipitation treatment, etc. according to a conventional manner.

The cleavage of the DNA isolated and purified from the microorganism can be carried out, for example, by ultrasonication or a restriction enzyme treatment. Preferably, a type II restriction enzyme specific to a particular nucleotide sequence is employed.

The vector for cloning is preferably a vector constructed from a phage or a plasmid for gene recombination that proliferates autonomously in a host microorganism. Examples of the phages include Lambda gt10, Lambda gt11 and the like, for example, when *Escherichia coli* is used as the host microorganism. Examples of the plasmids include PBR322, PUC19, pBluescript and the like, when *Escherichia coli* is used as the host microorganism.

While a vector fragment can be obtained during cloning by cleaving such a vector with a restriction enzyme used for cleavage of the microbial DNA, i.e., the donor of the gene encoding the creatinine amide hydrolase mentioned above, the restriction enzyme is not limited to the same enzyme used for the cleavage of the microbial DNA. The microbial DNA fragment and the vector DNA fragment can be bound to each other by any of known methods using a DNA ligase and, for example, a recombinant vector of the microbial DNA fragment and the vector DNA fragment can be prepared by annealing the cohesive end of the microbial DNA fragment and the cohesive end of the vector fragment, followed by ligating the resultant with a suitable DNA ligase. If necessary, after annealing, the resultant can be introduced into a host microorganism and ligated by an intracellular DNA ligase to obtain a recombinant vector.

The host microorganism used in cloning is not particularly limited as far as the recombinant vector therein is stable, can proliferate autonomously, and allows gene expression of an exogenous gene. Specific examples thereof include *Escherichia coli* W3110, *Escherichia coli* C600, *Escherichia coli* HB101, *Escherichia coli* JM109, *Escherichia coli* DH5α, and the like.

As a method to be employed for introducing the recombinant vector into the host microorganism, there can be mentioned a competent cell method with a calcium treatment, an electroporation method, or the like, when the host microorganism is *Escherichia coli*.

The transformant microorganism thus obtained can stably produce a large amount of the creatinine amide hydrolase when cultured in a nutrient medium. The selection of introduction of the desired recombinant vector into the host microorganism can be carried out by screening the expression of a drug resistance marker present in the vector containing the desired DNA.

The nucleotide sequence of the creatinine amide hydrolase gene obtained by the above-mentioned method was decoded by the dideoxy method described in Science, 214, 1205 (1981). In addition, the amino acid sequence of the creatinine amide hydrolase was deduced from the nucleotide sequence thus determined.

The creatinine amide hydrolase gene contained in the recombinant vector once selected as mentioned above can be incorporated easily into a recombinant vector that can be replicated in a microorganism having a creatinine amide hydrolase-producing capability by recovering the DNA of the creatinine amide hydrolase gene from the recombinant vector containing the creatinine amide hydrolase gene with a restriction enzyme and a PCR method and ligating it with another vector fragment. Transformation of the microorganism having creatinine amide hydrolase-producing capability with such a vector can be carried out, for example, by a competent cell method with a calcium treatment or an electroporation method.

The present invention also relates to a method for producing a modified creatinine amide hydrolase by culturing a transformant transformed with a vector containing a gene encoding the modified creatinine amide hydrolase.

In addition, another aspect of the present invention includes a method for producing a creatinine amide hydrolase whose Km value to creatinine is decreased as compared with that of a corresponding wild-type enzyme, which comprises subjecting a creatinine amide hydrolase to the amino acid mutagenesis according to any one of claims 1 to 9.

The creatinine amide hydrolase of the present invention can be produced by culturing the transformant thus obtained.

For example, the transformant microorganism thus obtained can produce a large amount of the modified protein reliably when cultured in a nutrient medium. The culture conditions of the transformant, i.e., the host microorganism can be determined by taking the nutritional physiological properties of the host microorganism into consideration, and the culture is carried out in a liquid culture medium in most cases. Aerobic culture with agitation or stirring is advantageous in the industrial production.

A wide variety of nutrients commonly used in microbial culture are used as nutrient sources of the culture medium. As a carbon source, any assimilable carbon compounds can be used, and examples thereof include glucose, sucrose, lactose, maltose, lactose, molasses, pyruvic acid, and the like. Further, as a nitrogen source, any available nitrogen compounds can be used, and examples thereof include peptone, meat extract, yeast extract, casein hydrolysate, soybean dregs alkali extract, and the like. In addition, salts such as a phosphate salt, a carbonate salt, a sulfate salt, and salts of magnesium, calcium, potassium, iron, manganese and zinc, particular amino acids, particular vitamins and the like are used, if necessary.

The cultivation temperature can be varied appropriately in a range allowing the growth of the microorganisms and the production of the modified creatinine amide hydrolase. However, in the case of a microorganism having creatinine amide hydrolase-producing capability, the temperature is preferably about 20 to 42° C. The cultivation period varies to some extent according to conditions. However, the cultivation is appropriately terminated by choosing a time when the modified creatinine amide hydrolase reaches a maximum yield. Usually, the cultivation is carried out for about 6 to 48 hours. The pH of the culture medium can vary appropriately in a range allowing the growth of the microorganism and the production of the modified creatinine amide hydrolase. However, preferably, the pH is in a range of about 6.0 to 9.0.

The culture containing the modified creatinine amide hydrolase-producing microorganism can be collected and used as such. However, in general, when the modified creatinine amide hydrolase is present in the culture, the culture is separated into a solution containing the modified creatinine amide hydrolase and the microbial cells, for example, by filtration or centrifugation according to a conventional method, and then the solution is used. If the modified creatinine amide hydrolase is present in the microbial cells, the microbial cells are separated from the culture obtained, for example, by means of filtration or centrifugation and then ruptured, for example, by a mechanical method or an enzymatic method with, for example a lysozyme and, if necessary, adding a chelating agent such as EDTA and a surfactant thereto for solubilization of the creatinine amide hydrolase to obtain the enzyme as an aqueous solution.

The creatinine amide hydrolase-containing solution thus obtained can, for example, be concentrated under reduced pressure or by membrane filtration or precipitated by salting out, for example with ammonium sulfate or sodium sulfate, or by fractional precipitation with a hydrophilic organic solvent such as methanol, ethanol or acetone. In addition, a heat treatment and an isoelectric point treatment are also effective purification processes. Then, the purified creatinine amide hydrolase can be obtained by carrying out gel filtration with an adsorbent or a gel filtration agent, adsorption chromatography, ion exchange chromatography, and/or affinity chromatography.

For example, the purified creatinine amide hydrolase product can be obtained by gel filtration with Sephadex (Sephadex) gel (GE Healthcare Biosciences) and/or column chromatography with DEAE Sepharose CL-6B (GE Healthcare Biosciences), octyl Sepharose CL-6B (GE Healthcare Biosciences), or the like to separate and purify the enzyme. Preferably, the purified enzyme product is purified to such an extent that a single band is observed in electrophoresis (SDS-PAGE).

The purified enzyme thus obtained can be converted into a powder, for example, by freeze drying, vacuum drying, or spray dry and marketed it. At that time, the purified enzyme can be used by dissolving it in a phosphate buffer solution, a Tris hydrochloride buffer solution or a GOOD buffer solution. Preferred is a GOOD buffer solution, and in particular, a buffer solution of PIPES, MES or MOPS is particularly preferred. The creatinine amide hydrolase can be further stabilized by addition of an amino acid such as glutamic acid, glutamine, or lysine and other additives such as serum albumin.

The method for producing the modified protein of the present invention is not particularly limited, but the modified protein can be preferably produced by the following procedure. As a modifying method of an amino acid sequence constituting a protein, a conventional method for modifying genetic information can be employed. That is, a DNA containing the genetic information of the modified protein is produced by changing one or more particular bases of the DNA carrying the genetic information of the protein, or by inserting or deleting one or more particular bases thereof. Examples of a Specific method for modifying a base in a DNA include the use of a commercially available kit (Transformer Mutagenesis Kit manufactured by Clonetech, EXOIII/Mung Bean Deletion Kit manufactured by Stratagene, Quick Change Site Directed Mutagenesis Kit manufactured by Stratagene, etc.) and the use of a polymerase chain reaction (PCR) method.

In the present invention, by aiming at the 44th, 122nd, 179th, 180th, and 181st positions of the amino acid sequence of the creatinine amide hydrolase shown in SEQ ID No. 2, mutation was introduced at these amino acid sites by using the above-mentioned mutagenesis kit to prepare a library of random mutants and screening of the mutants was carried out by using the change in substrate specificity as an indicator. As a result, the modified creatinine amide hydrolase having a significant decrease in Km value to creatinine could be obtained.

An yet another aspect of the present invention is a reagent for determination of creatinine comprising a creatinine amide hydrolase having a Km value to creatinine of 55 mM or less, a creatine amidinohydrolase, a sarcosine oxidase, and a hydrogen peroxide-detecting reagent.

Example of the hydrogen peroxide-detecting reagent include peroxidase, 4-aminoantipyrine, and Trinder's reagent.

One aspect of the reagent for determination of creatinine includes a composition for determination of creatinine comprising the modified creatinine amide hydrolase described in any one of claims 1 to 13.

One aspect of the reagent for determination of creatinine includes a kit for determination of creatinine comprising the modified creatinine amide hydrolase described in any one of claims 1 to 13.

The determination method of the present invention uses the following reactions.

(a) Reaction for formation of creatine from creatinine and water by creatinine amide hydrolase (Creatinine Amide Hydrolase)

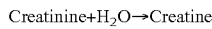

Creatinine+$H_2O$→Creatine (b) Reaction for formation of sarcosine and urea from creatine obtained in (a) and water by creatine amidinohydrolase (Creatine Amidinohydrolase)

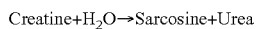

Creatine+$H_2O$→Sarcosine+Urea (c) Reaction for formation of glycine, formaldehyde and hydrogen peroxide from sarcosine obtained in (b), water and oxygen by sarcosine oxidase (Sarcosine Oxidase)

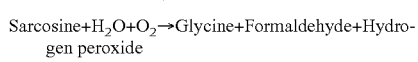

Sarcosine+$H_2O$+$O_2$→Glycine+Formaldehyde+Hydrogen peroxide (d) Reaction for detecting hydrogen peroxide obtained in (c)

For example, reaction for formation of a quinone dye and water from hydrogen peroxide obtained in (c), 4-aminoantipyrine and Trinder's reagent by a peroxidase (Peroxidase)

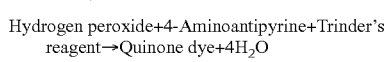

Hydrogen peroxide+4-Aminoantipyrine+Trinder's reagent→Quinone dye+4$H_2O$

In the determination method of the present invention, a creatinine amide hydrolase having a Km value to creatinine of 55 mM or less is used.

Examples of the origin of such a creatinine amide hydrolase include microorganisms of the genera *Pseudomonas, Alcaligenes, Corynebacterium, Arthrobacter, Flavobacterium, Micrococccus*, etc. and preferred hydrolases to be used include, but are not particularly limited to, those described in paragraphs [0012] to [0055] and Comparative Examples herein.

Examples of specimens used in the creatinine determination of to the present invention include biological samples such as blood serum, urine and plasma, but are not limited thereto.

In the reagent of the present invention, a composition can be in various forms such as liquid (aqueous solution, suspension, etc.), powder, or freeze dried powder. The freeze drying method is not particularly limited, and freeze drying can be carried out by a conventional method. The composition containing the enzyme of the present invention is not limited to a freeze dried powder, and can be used in the form of a solution obtained by re-dissolution of the freeze dried powder.

In each of the above-mentioned forms, the reagent composition of the present invention can be in a purified state or in a mixed state according to its shape and application, and if necessary, other various additives, for example, a surfactant, a stabilizer, a excipient can be added.

The method for blending such additives to the reagent of the present invention is not particularly limited. Examples thereof include a method for blending a stabilizer into a creatinine amide hydrolase-containing buffer solution, a method for blending creatinine amide hydrolase into a stabilizer-containing buffer solution, a method of blending creatinine amide hydrolase and a stabilizer into a buffer solution simultaneously, and the like.

The origin of the creatine amidinohydrolase to be used in the present invention is not particularly limited. For example, the creatine amidinohydrolase of *Arthrobacter* or *Alcaligenes* origin can be used. As commercially available products, "CRH-221" produced by Toyobo Co., Ltd., "Creatinase (C2-AT)" produced by Kikkoman Corporate, and the like can be used.

The origin of the sarcosine oxidase to be used in the present invention is not particularly limited. For example, sarcosine oxidase of *Corynebacterium* or *Arthrobacter* origin can be used. Commercially available products to be used include "SAO-341" produced by Toyobo Co., Ltd., "Sarcosine Oxidase (SOD-TE)" produced by Kikkoman Corporate, and the like.

The enzyme concentration of the creatinine amide hydrolase to be use in the present invention is not particularly limited as far as it is suitable for determination but, preferably, in a range of 1 to 1,000 U/mL.

The enzyme concentration of the creatinine amidinohydrolase is not particularly limited as far as it is suitable for determination but, preferably, in a range of 1 to 1,000 U/mL.

The enzyme concentration of the sarcosine oxidase is not particularly limited as far as it is suitable for determination but, preferably, in a range of 1 to 1000 U/mL.

The origin of the peroxidase to be used in the present invention is not particularly limited. For example, a peroxidase of horseradish origin is used. Commercially available products to be used include "PEO-301" produced by Toyobo Co., Ltd., and the like.

The reagent for determination of creatinine of the present invention contains, in addition to the above components, a buffer agent such as a phosphate salt, a GOOD buffer or a Tris buffer. Further, it can contain a chelating reagent for capturing enzymatic reaction interfering ions such as EDTA or O-dianisidine, ascorbate oxidase for removal of ascorbic acid, which is an interfering substance in quantitative determination of hydrogen peroxide, various surfactants such as Triton X-100 and NP-40, various antibacterial and antiseptic substances such as streptomycin and sodium azide, and the like. Various commercially available reagents can be used as these additives.

The reagent can be a single reagent or a combination of two or more reagents, but a single reagent, which is simpler and easier in handling, is more preferable in view of the advantages of the present invention. Further, a liquid reagent, which is simpler and easier in handling, is more preferable in view of the advantages of the present invention.

The buffer solution contained is not particularly limited, but, preferable are a Tris buffer solution, a phosphate buffer solution, a borate buffer solution, a GOOD buffer solution and the like. The pH of the buffer solution is adjusted in a range of about 5.0 to 10.0 according to particular application.

The content of the buffer agent in the freeze dried product is not particularly limited, but it is used preferably in a range of 0.1% (by weight) or more, particularly preferably 0.1 to 30% (by weight).

In addition, serum albumin can be added. When serum albumin is added to the above-mentioned aqueous composition, the content is preferably 0.05 to 0.5% by weight.

Examples of the albumin to be used include bovine serum albumin (BSA), ovalbumin (OVA), and the like. BSA is particularly preferable. The content of the albumin is preferably in a range of 1 to 80% (by weight), more preferably 5 to 70% (by weight).

On the other hand, in each embodiment mentioned above, the modified creatinine amide hydrolase, the composition for determination of creatinine and the kit for determination of creatinine of the present invention can take such a composition that it does not contain proteins other than protein components of the host origin.

Examples of the protein components other than those of the host origin include biological substances such as BSA.

By taking such a composition, it is considered that nonspecific reactions in the creatinine determination system can be decreased.

The buffer agent to be use can be a conventional buffer agent and, usually, a buffer capable of adjusting the pH of the composition to 5 to 10 is preferably used. More preferably, examples of the buffer agent include buffer agents such as boric acid and acetic acid, and GOOD buffer agents such as BES, Bicine, Bis-Tris, CHES, EPPS, HEPES, HEPPSO, MES, MOPS, MOPSO, PIPES, POPSO, TAPS, TAPSO, TES, and Tricine.

The content of the buffer agent (W/W) in a powder composition is preferably 1.0% to 50%.

In addition, an amino acid or an organic acid can be added to a composition essentially consisting of the modified creatinine amide hydrolase and a buffer agent. The composition may be an aqueous composition or a freeze dried product as far as it contains these components.

Any buffer agent having sufficient buffering capability in a pH range of 6.5 to 8.5 can be used as the buffer agent to be used in the present invention. Examples of the buffer agent in the above pH range include a phosphate salt, Tris, bis-Tris propane, N-tris(hydroxymethyl)methyl-2-aminoethanesulfonic acid (TES), and 3-(N-tris(hydroxymethyl)methylamino]-2-hydroxypropanesulfonic acid (TAPSO). Preferred is a phosphate salt buffer because of its low price and high stability. A preferable concentration range is 20 to 200 mM of a phosphate salt, and the preferable pH is 7 to 8.

In the present invention, the reagent for detection of hydrogen peroxide derived from creatinine is not particularly limited as far as it is a reagent which can detect hydrogen peroxide derived from creatinine, and preferably, it is a peroxidase and hydrogen peroxide-coloring reagent. The peroxidase and the hydrogen peroxide-coloring reagent are not particularly limited. Preferred is an indicator that is stable in a solution with low bilirubin interference.

Examples of the hydrogen peroxide-coloring reagent to be used include a combination of:

(1) 4-aminoantipyrine or 3-methyl-2-benzothiazoline hydrazone (MBTH) and (2) phenol or a derivative thereof, or aniline or a derivative thereof.

Examples of the phenol derivative include 2-chlorophenol, 4-chlorophenol, 1,2-dichlorophenol and the like.

Examples of the aniline derivative include N,N-dimethylaniline, N,N-diethylaniline, N,N-diethyl-m-toluidine, N,N-dimethyl-m-anisidine, N-ethyl-N-(3-methylphenyl)-N'-acetylethylenediamine, N-ethyl-N-(β-hydroxyethyl)-m-toluidine, N-ethyl-N-(2-hydroxy-3-sulfopropyl)-m-toluidine, N-ethyl-N-sulfopropyl-m-toluidine, N-ethyl-N-sulfopropyl-3,5-dimethoxyaniline, N-ethyl-N-(2-hydroxy-3-sulfopropyl)-3,5-dimethoxyaniline, N-ethyl-N-sulfopropyl-m-anisidine, N-ethyl-N-(3-methylphenyl)-N'-succinylethylenediamine, N-ethyl-N-(2-hydroxy-N-sulfopropyl)-m-anisidine, and the like.

In addition, a leuco dye such as 10-X-methylcarbamoyl-3,7-dimethylamino-10H-phenothiazine, bis[8-bis(4-chlorophenyl)methyl-4-dimethylaminophenyl]amine or 1,4-bis(dimethylamino)propyldiphenyl-(2,7-dihydroxy-4-naphthyl)methane can be used.

Various commercially available reagents are available for this purpose.

Examples of the indicator preferably used in detection of hydrogen peroxide derived from creatinine in the present invention include benzidines, leuco dyes, 4-aminoantipyrine, phenols, naphthols and aniline derivatives. More preferable indicators are 4-aminoantipyrine and N-ethyl-N-(2-hydroxy-3-sulfopropyl)-m-toluidine (TOOS). The preferable concentration range is 0.05 to 10 mM for 4-aminoantipyrine and 0.05 to 10 mM for TOOS.

The peroxidase used in detection of hydrogen peroxide derived from creatinine in the present invention is preferably a horseradish peroxidase because high-purity and low-priced commercial products are available. The enzyme concentration should be high enough for a rapid and complete reaction, and is thus, preferably 1,000 to 50,000 U/L.

Ferrocyanide can be added to the reagent so as to minimize the bilirubin interference. However, the presence of metal ions such as ferrocyanide may destabilize the indicator and the enzyme. The stability of the reagent of the present invention is high enough to allow addition of the ferrocyanide. A preferable concentration range of the ferrocyanide is 1 to 400 µM and the maximum concentration is a concentration at which the enzyme activity is inhibited.

An inactive protein can be added for further improvement of the stability of the reagent. The inactive proteins include serum albumins, globulins and fibrous proteins. A preferable protein is bovine serum albumin, and the preferable concentration thereof (wt/vol) is 0.05 to 1%. A lower concentration may be useful. A preferable inactive protein is a protein not containing protease impurities that cause enzyme decomposition.

The creatinine concentration is determined by using a given volume of a sample and a give volume of the reagent. The absorbance is measured as soon as possible after mixing for determination of a sample blank before significant change in the absorbance by creatinine metabolism. The first absorbance measurement is preferably carried out in the period of 0.5 to 5 seconds after mixing. The second absorbance measurement is carried out after the absorbance becomes constant, typically after 3 to 5 minutes when the reaction is carried out at a creatinine concentration of 5 mg/dL at 37° C. Typically, the reagent is standardized with an aqueous or blood serum solution having a known creatinine concentration.

The method for determining creatinine by using the reagent composition for determination of creatinine of the present invention comprising reacting a sample with a reagent containing the creatinine amide hydrolase, creatine amidinohydrolase, sarcosine oxidase, peroxidase, 4-aminoantipyrine and Trinder's reagent and determining the color intensity of the resulting quinone dye.

In another embodiment, the present invention includes a method for determining creatinine by using the modified creatinine amide hydrolase according to any one of claims 1 to 13.

The present invention also includes a method for improving the determination reactivity in a creatinine determination system comprising using the amino acid-mutated creatinine amide hydrolase according to any one of claims 1 to 13 in a creatinine amide hydrolase-utilizing creatinine determination system.

The present invention also includes a method for producing a determination reactivity-improved creatinine determination composition comprising the amino acid-mutated creatinine amide hydrolase according to any one of claims 1 to 13 in a creatinine amide hydrolase-utilizing creatinine determination system.

As will be described in Examples hereinafter, the modified creatinine amide hydrolase of the present invention has a Km value to creatinine significantly lower than that of a wild-type creatinine amide hydrolase. This suggests that it is possible to decrease an amount of the creatinine amide hydrolase used in, for example, creatinine determination of clinical samples, and thus to decrease the cost of the determination.

EXAMPLES

Hereinafter, the present invention will be described more specifically with reference to Examples.

Example 1

Preparation of Modified Creatinine Amide Hydrolase Gene

A chromosomal DNA of *Pseudomonas putida* PS-7 strain was prepared, and then an expression plasmid pCNH5-13 containing the creatinine amide hydrolase gene originated from that strain was prepared according to the methods described in Japanese Patent No. 2527035, and Biosci. Biotech. Biochem., 59, 7, p. 1331-1332 (1995).

The expression plasmid pCNH5-13 of a wild-type creatinine amide hydrolase is a plasmid obtained by inserting a structural gene encoding a creatinine amide hydrolase of *Pseudomonas putida* PS-7 strain origin into a multicloning site of vector pBluescript SK(−). The nucleotide sequence is represented by SEQ ID No. 2 in Sequence Listing, and the amino acid sequence of the creatinine amide hydrolase deduced from the nucleotide sequence is represented by SEQ ID No. 1 in Sequence Listing.

Then, mutagenesis was carried out by using PCNH5-13, a synthetic oligonucleotide of SEQ ID No. 3 shown in the Sequence Listing and a synthetic oligonucleotide complementary thereto, and by using a QuickChange™ site-Directed Mutagenesis Kit (trade name, manufactured by STRATAGENE) according to its protocol, followed by determination of the nucleotide sequence to obtain a recombinant plasmid (pCNHM1) encoding a mutant creatinine amide hydrolase wherein the 179th glycine in the amino acid sequence of SEQ ID No. 2 was substituted with serine.

According to the same manner as mentioned above, mutagenesis was carried out by using PCNH5-13, a synthetic oligonucleotide of SEQ ID No. 4 shown in the Sequence Listing and a synthetic oligonucleotide complementary thereto, and by using a QuickChange™ site-Directed Mutagenesis Kit (trade name, manufactured by STRATAGENE) to obtain a recombinant plasmid (pCNHM2) encoding a mutant creatinine amide hydrolase wherein the 179th glycine in the amino acid sequence of SEQ ID No. 2 is substituted with alanine.

According to the same manner as mentioned above, mutagenesis was carried out by using PCNH5-13, a synthetic oligonucleotide of SEQ ID No. 5 shown in the Sequence Listing and a synthetic oligonucleotide complementary thereto, and by using a QuickChange™ site-Directed Mutagenesis Kit (trade name, manufactured by STRATAGENE) to obtain a recombinant plasmid (pCNHM3) encoding a mutant creatinine amide hydrolase wherein the 180th glycine in the amino acid sequence of SEQ ID No. 2 is substituted with alanine.

According to the same manner as mentioned above, mutagenesis was carried out by using PCNH5-13, a synthetic oligonucleotide of SEQ ID No. 6 shown in the Sequence Listing and a synthetic oligonucleotide complementary thereto, and by using a QuickChange™ site-Directed Mutagenesis Kit (trade name, manufactured by STRATAGENE) to obtain a recombinant plasmid (pCNHM4) encoding a mutant creatinine amide hydrolase wherein the 180th glycine in the amino acid sequence of SEQ ID No. 2 is substituted with serine.

According to the same manner as mentioned above, mutagenesis was carried out by using PCNH5-13, a synthetic oligonucleotide of SEQ ID No. 7 shown in the Sequence Listing and a synthetic oligonucleotide complementary thereto, and by using a QuickChange™ site-Directed Mutagenesis Kit (trade name, manufactured by STRATAGENE) to obtain a recombinant plasmid (pCNHM5) encoding a mutant creatinine amide hydrolase wherein the 181st valine in the amino acid sequence of SEQ ID No. 2 is substituted with isoleucine.

According to the same manner as mentioned above, mutagenesis was carried out by using PCNH5-13, a synthetic oligonucleotide of SEQ ID No. 8 shown in the Sequence Listing and a synthetic oligonucleotide complementary thereto, and by using a QuickChange™ site-Directed Mutagenesis Kit (trade name, manufactured by STRATAGENE) to obtain a recombinant plasmid (pCNHM6) encoding a mutant creatinine amide hydrolase wherein the 44th aspartic acid in the amino acid sequence of SEQ ID No. 2 is substituted with arginine.

According to the same manner as mentioned above, mutagenesis was carried out by using PCNH5-13, a synthetic oligonucleotide of SEQ ID No. 9 shown in the Sequence Listing and a synthetic oligonucleotide complementary thereto, and by using a QuickChange™ site-Directed Mutagenesis Kit (trade name, manufactured by STRATAGENE) to obtain a recombinant plasmid (pCNHM7) encoding a mutant creatinine amide hydrolase wherein the 44th aspartic acid in the amino acid sequence of SEQ ID No. 2 is substituted with glycine.

According to the same manner as mentioned above, mutagenesis was carried out by using PCNH5-13, a synthetic oligonucleotide of SEQ ID No. 10 shown in the Sequence Listing and a synthetic oligonucleotide complementary thereto, and by using a QuickChange™ site-Directed Mutagenesis Kit (trade name, manufactured by STRATAGENE) to obtain a recombinant plasmid (pCNHM8) encoding a mutant creatinine amide hydrolase wherein the 44th aspartic acid in the amino acid sequence of SEQ ID No. 2 is substituted with serine.

According to the same manner as mentioned above, mutagenesis was carried out by using PCNH5-13, a synthetic oligonucleotide of SEQ ID No. 12 shown in the Sequence Listing and a synthetic oligonucleotide complementary thereto, and by using a QuickChange™ site-Directed Mutagenesis Kit (trade name, manufactured by STRATAGENE) to obtain a recombinant plasmid (pCNHM9) encoding a mutant creatinine amide hydrolase wherein the 122nd glutamic acid in the amino acid sequence of SEQ ID No. 2 is substituted with aspartic acid.

Example 2

Preparation of Modified Creatinine Amide Hydrolase

*Escherichia coli* DH5α competent cells were transformed with each recombinant plasmid, pCNHM1, pCNHM2, pCNHM3, pCNHM4, pCNHM5, pCNHM6, pCNHM7, pCNHM8 or pCNHM9, to obtain the correspondent transformant.

Five ml of CNH-producing medium (1% polypeptone, 2% yeast extract, 1% sodium chloride, and 5 mM manganese chloride) was placed in a test tube and sterilized in an autoclave at 121° C. for 20 minutes. After cooling by standing, ampicillin separately sterilized by filtration was added thereto so that its concentration became 100 μl/ml. A single colony of *Escherichia coli* DH5α (pCNHM1) previously cultured in a LB agar medium containing 100 μl/ml ampicillin at 37° C. for 16 hours was inoculated thereinto, followed by culturing aerobically with stirring at 37° C. for 22 hours.

The microbial cells were collected by centrifugation, suspended in a 50 mM potassium phosphate buffer solution (pH 7.5), ruptured by ultrasonication and centrifuged to obtain the supernatant as a crude enzyme solution. The mutant was designated as CNHM1.

According to the same manner as mentioned above, *Escherichia coli* DH5α transformant with each recombinant plasmid pCNHM2, pCNHM3, pCNHM4, pCNHM5, pCNHM6, pCNHM7, pCNHM8, pCNHM9 or pCNHM10 was prepared to obtain the corresponding purified enzyme product. The enzyme products obtained were designated as CNHM2, CNHM3, CNHM4, CNHM5, CNHM6, CNHM7, CNHM8, and CNHM9, respectively.

Comparative Example 1

Preparation of Wild-Type Creatinine Amide Hydrolase

As a Comparative Example, according to the same manner as mentioned above, *Escherichia coli* DH5α transformant with PCNH5-13 was prepared to obtain a purified enzyme product before modification.

Example 3

Evaluation of Modified Creatinine Amide Hydrolase 1

Each of the various creatinine amide hydrolases including the mutant creatinine amide hydrolases (CNHM1, CNHM2, CNHM3, CNHM4, CNHM5, CNHM6, CNHM7, CNHM8 and CNHM9) obtained in Example 2 and that obtained in Comparative Example 1 was added to a 50 mM potassium phosphate buffer solution (pH 7.5) so that the concentration became 1.67 U/mL, and the creatinine amide hydrolase activity was determined by the activity determination method an mentioned above. The results are summarized in Table 1. As seen from Table 1, it was confirmed that the modified creatinine amide hydrolases of the present invention have a Km value smaller as compared with that of the enzyme before modification.

In Examples 1 to 3, the activity of the creatinine amide hydrolase was determined in the following manner. As for the enzyme activity in the present invention, a unit (U) of the enzyme is defined as the amount of the enzyme required for generating 1 μmole of creatine per minute under the following conditions.

Composition of Reaction Mixture

R1

0.58 M HEPES, pH 8

0.005% 4-Aminoantipyrine 0.015% Phenol

60 U/ml Creatine amidinohydrolase

12 U/ml Sarcosine oxidase

6 U/mL Peroxidase

R2

0.25 M Creatinine 0.27N HCl

The determination was carried out by mixing 200 μl of R1, 60 μl of R2 and 10 μl of the enzyme solution, followed by reaction at 37° C. for 10 minutes. Then, the change in absorbance at 505 nm was measured by using a HITACHI7060 automatic analyzer.

The following Table 1 summarizes the Km values to creatinine of the novel creatinine amidohydrolases of the present invention and the wild-type creatinine amidohydrolase. As seen from Table 1, the novel creatinine amidohydrolases of the present invention have a Km value lower than that of the wild-type creatinine amidohydrolase.

TABLE 1

| Enzyme | Km (mM) |
| --- | --- |
| Wild-type | 81 |
| CNHM1 | 16 |
| CNHM2 | 28 |
| CNHM3 | 27 |
| CNHM4 | 35 |
| CNHM5 | 49 |
| CNHM6 | 49 |
| CNHM7 | 53 |
| CNHM8 | 50 |
| CNHM9 | 37 |

Example 4

Evaluation of the Reactivity of the Reagent for Determination of Creatinine Using Modified Creatinine Amide Hydrolase 100 μl/mL of the mutant creatinine amide hydrolase (CNHM1) obtained in Example 2 was added to the above-mentioned second reagent to prepare a liquid reagent for determination of creatinine (reagent of the present invention). 100 U/mL of a wild-type creatinine amide hydrolase Pseudomonas putida origin (product code: CNH-311, manufactured by Toyobo Co., Ltd.) was added to the above-mentioned second reagent to obtain a liquid reagent for determination of creatinine (reagent of Comparative Example) as a control.

Figure 1:
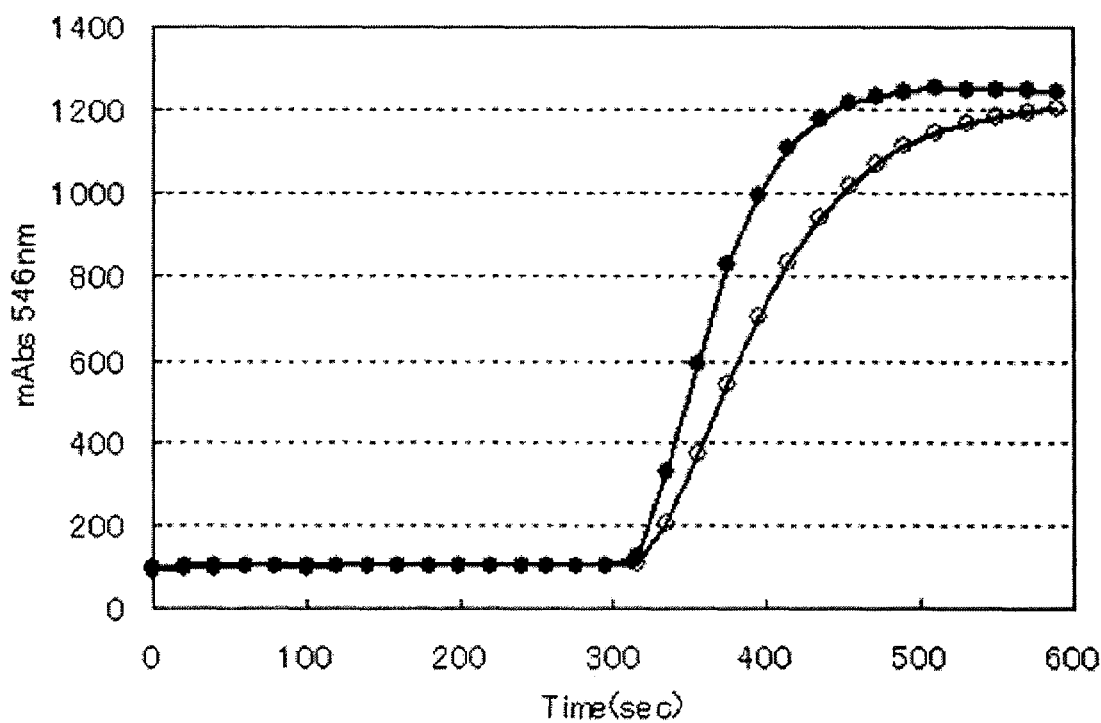
FIG. 1 illustrates the results of reactivity evaluation of the reagent of present invention and the reagent of Comparative Example.

The reactivities of the reagent of the present invention and the reagent of Comparative Example were compared by the determination using 5 mg/dL of creatinine. As shown in FIG. 1, the reagent of the present invention had a shortened period required for reaching the end point.

Example 5

Amount of the Modified Creatinine Amide Hydrolase Required for the Same Reactivity as that of the Wild-Type Enzyme 100 U/mL of the mutant creatinine amide hydrolase (CNHM1) obtained in Example 2 was added to the above mentioned second reagent to prepare a liquid reagent for determination of creatinine (reagent of the present invention reagent). As a control, 400 U/mL of a wild-type creatinine amide hydrolase of Pseudomonas putida origin (product code: CNH-311, manufactured by Toyobo Co., Ltd.) was added to the above mentioned second reagent to prepare a liquid reagent for determination of creatinine (reagent of Comparative Example) as a control.

The reactivities of the reagent of the present invention and the reagent of Comparative Example were compared by the determination using 5 mg/dL creatinine. As shown in FIG. 2, the unit of the creatinine amide hydrolase of the reagent of the present invention was ¼ of that of the reagent of Comparative Example at a creatinine amide hydrolase for obtaining the same reactivity.

In Examples 4 and 5, 5 mg/dl creatinine was measured by the following method using the first and the second reagents having the following compositions.

The First Reagent 50 mM MOPS buffer solution (pH 7.5)

mM NaCl 0.1% Triton X-100

0.14 g/l TOOS

60 U/mL Creatine amidinohydrolase (CRH-221, produced by Toyobo Co., Ltd.)

16 U/mL Sarcosine oxidase (SAO-351, produced by Toyobo Co., Ltd.)

The Second Reagent 50 mM MOPS buffer solution (pH 7.5)

0.1% Triton X-100

10 U/mL Peroxidase (PEO-301, produced by Toyobo Co., Ltd.)

0.6 g/l 4-Aminoantipyrine

The abbreviation is as follows:

TOOS: N-ethyl-N-(2-hydroxy-3-sulfopropyl)-3-methoxyaniline

Determination Method

Hitachi 7060 automatic analyzer was used. 270 μL of the first reagent was added to 6 μL of a sample, and the mixture was incubated at 37° C. for 5 minutes to carry out the first reaction. Then, 90 μL of the second reagent was added thereto, and the mixture was incubated for 5 minutes, to carry out the second reaction. The absorbances at 546 nm of the first and second reactions were determined by a two-end point method wherein the difference between the absorbances after liquid volume correction was made. The creatinine concentration of a sample whose creatinine concentration was unknown was calculated from the absorbances of purified water and an aqueous 5 mg/dL creatinine solution.

INDUSTRIAL APPLICABILITY

The present invention provides a creatinine amide hydrolase having improved affinity for a substrate. The modified creatinine amide hydrolase can be utilized as a reagent for determination of creatinine. In addition, according to the present invention, it is possible to reduce the amount of an enzyme to be used in a quantitative analysis of creatinine to ¼ of that of a conventional analysis. Further, it is also possible to reduce the determination period of time and thus to increase the number of samples to be analyzed because the reaction time required to reach an end point is shortened when using the same amount of the enzyme as that in a conventional analysis.

The invention claimed is:

1. An isolated modified creatinine amide hydrolase comprising the amino acid sequence of SEQ ID NO: 2, except that an amino acid at one or more positions selected from the group consisting of the 44th, 122nd, 179th, 180th, and 181st positions thereof is substituted with a different amino acid.

2. The modified creatinine amide hydrolase according to claim 1, wherein glycine at the 179th position of the amino acid sequence of SEQ ID NO: 2 is substituted with serine.

3. The modified creatinine amide hydrolase according to claim 1, wherein glycine at the 179th position of the amino acid sequence of SEQ ID NO: 2 is substituted with alanine.

4. The modified creatinine amide hydrolase according to claim 1, wherein glycine at the 180th position of the amino acid sequence of SEQ ID NO: 2 is substituted with alanine.

5. A reagent for determination of creatinine, comprising the modified creatinine amide hydrolase according to claim 1.

6. A method for determining the level of creatinine in a test sample which comprises
   (a) providing a test sample,
   (b) contacting the test sample with the modified creatinine amide hydrolase according to claim 1, creatinine amidinohydrolase, and sarcosine oxidase, so as to produce hydrogen peroxide, and
   (c) detecting the level of hydrogen peroxide,
   wherein the level of hydrogen peroxide correlates with the level of creatinine in the test sample.

7. A reagent for determination of creatinine, comprising the modified creatinine amide hydrolase according to claim 2.

8. A reagent for determination of creatinine, comprising the modified creatinine amide hydrolase according to claim 3.

9. A reagent for determination of creatinine, comprising the modified creatinine amide hydrolase according to claim 4.

10. A method for determining the level of creatinine in a test sample which comprises
    (a) providing a test sample,
    (b) contacting the test sample with the modified creatinine amide hydrolase according to claim 2, creatinine amidinohydrolase, and sarcosine oxidase, so as to produce hydrogen peroxide, and
    (c) detecting the level of hydrogen peroxide,
    wherein the level of hydrogen peroxide correlates with the level of creatinine in the test sample.

11. A method for determining the level of creatinine in a test sample which comprises
    (a) providing a test sample,
    (b) contacting the test sample with the modified creatinine amide hydrolase according to claim 3, creatinine amidinohydrolase, and sarcosine oxidase, so as to produce hydrogen peroxide, and
    (c) detecting the level of hydrogen peroxide,
    wherein the level of hydrogen peroxide correlates with the level of creatinine in the test sample.

12. A method for determining the level of creatinine in a test sample which comprises
    (a) providing a test sample,
    (b) contacting the test sample with the modified creatinine amide hydrolase according to claim 4, creatinine amidinohydrolase, and sarcosine oxidase, so as to produce hydrogen peroxide, and
    (c) detecting the level of hydrogen peroxide,
    wherein the level of hydrogen peroxide correlates with the level of creatinine in the test sample.

13. The modified creatinine amide hydrolase according to claim 1, wherein the modified creatinine amide hydrolase consists of the amino acid sequence of SEQ ID NO: 2, except that an amino acid at one or more positions selected from the group consisting of the 44th, 122nd, 179th, 180th, and 181st positions thereof is substituted with a different amino acid.

14. The modified creatinine amide hydrolase according to claim 1, wherein the modified creatinine amide hydrolase comprises the amino acid sequence of SEQ ID NO: 2, except that an amino acid at a single position selected from the group consisting of the 44th, 122nd, 179th, 180th, and 181st positions thereof is substituted with a different amino acid.

15. The modified creatinine amide hydrolase according to claim 14, wherein glycine at the 179th position of the amino acid sequence of SEQ ID NO: 2 is substituted with serine.

16. The modified creatinine amide hydrolase according to claim 14, wherein glycine at the 179th position of the amino acid sequence of SEQ ID NO: 2 is substituted with alanine.

17. The modified creatinine amide hydrolase according to claim 14, wherein glycine at the 180th position of the amino acid sequence of SEQ ID NO: 2 is substituted with alanine.

18. A reagent for determination of creatinine, comprising the modified creatinine amide hydrolase according to claim 14.

19. A method for determining the level of creatinine in a test sample which comprises
    (a) providing a test sample,
    (b) contacting the test sample with the modified creatinine amide hydrolase according to claim 14, creatinine amidinohydrolase, and sarcosine oxidase, so as to produce hydrogen peroxide, and
    (c) detecting the level of hydrogen peroxide,
    wherein the level of hydrogen peroxide correlates with the level of creatinine in the test sample.

* * * * *

SEQUENCE LISTING

<160> NUMBER OF SEQ ID NOS: 12

<210> SEQ ID NO 1
<211> LENGTH: 1474
<212> TYPE: DNA
<213> ORGANISM: Pseudomonas putida

<400> SEQUENCE: 1

| | | | | | | |
|---|---|---|---|---|---|---|
| atgagcaaga | gtgtttttgt | aggtgagctg | acctggaagg | agtacgaggc | gcgtgtcgcg | 60 |
| gcaggtgact | gcgtgctcat | gctgccggtc | ggcgccctgg | aacagcacgg | ccatcacatg | 120 |
| tgcatgaacg | tcgatgtgct | gctgcccacg | gcggtgtgca | agcgggtcgc | cgagcgcatt | 180 |
| ggtgcgctgg | tcatgccggg | gctgcagtac | ggctacaagt | cccagcagaa | gtccggcggc | 240 |
| ggcaatcact | tccccggcac | caccagcctg | gatggcgcca | ccctgactgg | cacggtgcag | 300 |
| gacatcatcc | gcgagctggc | gcgccatggt | gcgcgtcgcc | tggtactgat | gaacggccac | 360 |
| tacgaaaatt | ccatgttcat | cgtcgaaggc | atcgacctcg | ccctgcgcga | gctgcgctat | 420 |
| gccggcatcc | aggacttcaa | agtggtggtg | ctctcctact | gggacttcgt | caaggacccg | 480 |
| gctgtgatcc | agcagctcta | tcccgagggc | ttcctcggct | gggacatcga | gcacggcggc | 540 |
| gtcttcgaga | cctccctgat | gctggctttg | tacccggacc | tggtggacct | ggaccgcgtc | 600 |
| gtcgatcacc | cacctgcaac | cttcccaccc | tatgacgtgt | tccggtcga | cccggcccgt | 660 |
| acgccggcgc | cgggcactct | gtcgtcggcg | aatgagcaag | agtgtttttg | taggtgagct | 720 |
| gacctggaag | gagtacgagg | cgcgtgtcgc | ggcaggtgac | tgcgtgctca | tgctgccggt | 780 |
| cggcgccctg | gaacagcacg | gccatcacat | gtgcatgaac | gtcgatgtgc | tgctgcccac | 840 |
| ggcggtgtgc | aagcgggtcg | ccgagcgcat | tggtgcgctg | gtcatgccgg | ggctgcagta | 900 |
| cggctacaag | tcccagcaga | agtccggcgg | cggcaatcac | ttccccggca | ccaccagcct | 960 |
| ggatggcgcc | accctgactg | gcacggtgca | ggacatcatc | cgcgagctgg | cgcgccatgg | 1020 |
| tgcgcgtcgc | ctggtactga | tgaacggcca | ctacgaaaat | tccatgttca | tcgtcgaagg | 1080 |
| catcgacctc | gccctgcgcg | agctgcgcta | tgccggcatc | caggacttca | aagtggtggt | 1140 |
| gctctcctac | tgggacttcg | tcaaggaccc | ggctgtgatc | cagcagctct | atcccgaggg | 1200 |
| cttcctcggc | tgggacatcg | agcacggcgg | cgtcttcgag | acctccctga | tgctggcttt | 1260 |
| gtacccggac | ctggtggacc | tggaccgcgt | cgtcgatcac | ccacctgcaa | ccttcccacc | 1320 |
| ctatgacgtg | tttccggtcg | acccggcccg | tacgccggcg | ccgggcactc | tgtcgtcggc | 1380 |
| gaagacggcc | agccgagaga | agggcgagtt | gatcctggag | gtctgcgtcc | agggcattgc | 1440 |
| cgacgctatc | cgcgaggagt | tcccgcccac | ctga | | | 1474 |

<210> SEQ ID NO 2
<211> LENGTH: 260
<212> TYPE: PRT
<213> ORGANISM: Pseudomonas putida

```
<400> SEQUENCE: 2

Met Ser Lys Ser Val Phe Val Gly Glu Leu Thr Trp Lys Glu Tyr Glu
 1               5                  10                  15

Ala Arg Val Ala Ala Gly Asp Cys Val Leu Met Leu Pro Val Gly Ala
            20                  25                  30

Leu Glu Gln His Gly His His Met Cys Met Asn Val Asp Val Leu Leu
        35                  40                  45

Pro Thr Ala Val Cys Lys Arg Val Ala Glu Arg Ile Gly Ala Leu Val
    50                  55                  60

Met Pro Gly Leu Gln Tyr Gly Tyr Lys Ser Gln Lys Ser Gly Gly
65                  70                  75                  80

Gly Asn His Phe Pro Gly Thr Thr Ser Leu Asp Gly Ala Thr Leu Thr
                85                  90                  95

Gly Thr Val Gln Asp Ile Ile Arg Glu Leu Ala Arg His Gly Ala Arg
            100                 105                 110

Arg Leu Val Leu Met Asn Gly His Tyr Glu Asn Ser Met Phe Ile Val
        115                 120                 125

Glu Gly Ile Asp Leu Ala Leu Arg Glu Leu Arg Tyr Ala Gly Ile Gln
    130                 135                 140

Asp Phe Lys Val Val Leu Ser Tyr Trp Asp Phe Val Lys Asp Pro
145                 150                 155                 160

Ala Val Ile Gln Gln Leu Tyr Pro Glu Gly Phe Leu Gly Trp Asp Ile
                165                 170                 175

Glu His Gly Gly Val Phe Glu Thr Ser Leu Met Leu Ala Leu Tyr Pro
            180                 185                 190

Asp Leu Val Asp Leu Asp Arg Val Val Asp His Pro Pro Ala Thr Phe
        195                 200                 205

Pro Pro Tyr Asp Val Phe Pro Val Asp Pro Ala Arg Thr Pro Ala Pro
    210                 215                 220

Gly Thr Leu Ser Ser Ala Lys Thr Ala Ser Arg Glu Lys Gly Glu Leu
225                 230                 235                 240

Ile Leu Glu Val Cys Val Gln Gly Ile Ala Asp Ala Ile Arg Glu Glu
                245                 250                 255

Phe Pro Pro Thr
            260

<210> SEQ ID NO 3
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 3
ggctgggaca tcgagcacag cggcgtcttc gagacctcc                              39

<210> SEQ ID NO 4
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 4
ggctgggaca tcgagcacgc aggcgtcttc gagacctcc                              39
```

```
<210> SEQ ID NO 5
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 5
tgggacatcg agcacggcgc cgtcttcgag acctccctg                              39

<210> SEQ ID NO 6
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 6
tgggacatcg agcacggcag cgtcttcgag acctccctg                              39

<210> SEQ ID NO 7
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 7
gacatcgagc acggcggcat cttcgagacc tccctgatg                              39

<210> SEQ ID NO 8
<211> LENGTH: 39
<212> TYPE: DNA
<213> ORGANISM: Artificial Sequence
<220> FEATURE:
<223> OTHER INFORMATION: Artificial Sequence oligonuceotide

<400> SEQUENCE: 8
catcacatgt gcatgaaccg cgatgtgctg ctgcccacg                              39

<210> SEQ ID NO 9
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 9
catcacatgt gcatgaacgg cgatgtgctg ctgcccacg                              39

<210> SEQ ID NO 10
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 10
catcacatgt gcatgaacag cgatgtgctg ctgcccacg                              39

<210> SEQ ID NO 11
<211> LENGTH: 39
<212> TYPE: DNA
<213> ORGANISM: Artificial Sequence
<220> FEATURE:
<223> OTHER INFORMATION: Artificial Sequence oligonucleotide
```

-continued

```
<400> SEQUENCE: 11
catcacatgt gcatgaacaa tattgtgctg ctgcccacg                    39

<210> SEQ ID NO 12
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 12
ctgatgaacg gccactacga caattccatg ttcatcgtc                    39
```